United States Patent [19]  [11] 4,016,215
Otsuki et al.  [45] Apr. 5, 1977

[54] STABILIZATION OF 1,1,1-TRICHLOROETHANE

[75] Inventors: Susumu Otsuki; Kanichi Uchida; Isao Miyanohara, all of Shin Nanyo, Japan

[73] Assignee: Toyo Soda Manufacturing Co., Ltd., Tokyo, Japan

[22] Filed: Feb. 21, 1975

[21] Appl. No.: 551,646

Related U.S. Application Data

[60] Continuation-in-part of Ser. No. 363,495, May 24, 1973, abandoned, which is a division of Ser. No. 169,112, Aug. 4, 1971, abandoned.

[30] Foreign Application Priority Data

Aug. 21, 1970  Japan .............................. 45-72813

[52] U.S. Cl. ....................................... 260/652.5 R
[51] Int. Cl.$^2$ ...................................... C07C 17/42
[58] Field of Search ............................ 260/652.5 R

[56] References Cited

UNITED STATES PATENTS

| 3,326,988 | 5/1967 | Stack | 260/652.5 R |
| 3,326,989 | 5/1967 | Cormany et al. | 260/652.5 R |
| 3,549,715 | 12/1970 | Cormany et al. | 260/652.5 R |
| 3,661,788 | 5/1972 | Campbell et al. | 260/652.5 R |

*Primary Examiner*—D. Horwitz
*Attorney, Agent, or Firm*—Oblon, Fisher, Spivak, McClelland & Maier

[57] ABSTRACT

1,1,1-trichloroethane is stabilized against decomposition initiated by contact with iron by the use of a combination of styrene oxide, phenyl glycidyl ether or mixtures thereof with a second conventional stabilizer of an alcohol, a nitro compound or a cyclic ether.

7 Claims, No Drawings

STABILIZATION OF 1,1,1-TRICHLOROETHANE

CROSS-REFERENCE TO RELATED APPLICATIONS

This application is a Continuation-In-Part of Application Ser. No. 363,495, filed May 24, 1973, now abandoned which is a Divisional of Application Ser. No. 169,112, filed Aug. 4, 1971.

BACKGROUND OF THE INVENTION

1. Field Of The Invention

This invention relates to a technique for stabilizing 1,1,1-trichloroethane against vapor or liquid phase decomposition caused by contact with metallic iron.

2. Description Of Prior Art 1,1,1-trichloroethane is known to be a superior solvent for grease, oils, tars and waxes and it is known to be generally non-flammable and less poisonous than other chlorinated hydrocarbons. Because of these desirable properties, 1,1,1-trichloroethane is frequently used as a grease-removing solvent for a variety of light and heavy metals. Its full industrial acceptance, however, has been somewhat limited, since it is easily decomposable when in contact with certain metals, and tends to generate corrosive amounts of hydrogen chloride. This decomposition reaction can occur even when the solvent is used as a cold liquid, although the reaction is more likely to occur at higher temperatures and especially in the hot vapor phase. This high tendency to decompose in the hot vapor phase has recently become an increasingly severe detriment, in view of the greater industrial use of vapor cleaning techniques for hot processing equipment.

Many stabilizers and stabilizing systems have been suggested to alleviate the extent of decomposition. It has been found, however, that the nature and degree of the decomposition reaction is dependent upon the particular metal being contacted. Stabilization of 1,1,1-trichloroethane against exposure to one type of metal will not necessarily be effective against exposure to a different metal. In fact, a stabilizer for contact with one metal, may actually act as an accelerator for decomposition when contacted with another metal.

A need exists, therefore, for a stabilizer or stabilizer system which is effective against decomposition caused by contact with a variety of different metals.

Iron is one of the several metals which is frequently in contact with 1,1,1-trichloroethane, since iron is frequently used as an element in forming anti-corrosion processing equipment.

It would be desirable, therefore, to provide a stabilizer or stabilizer system which is particularly effective for stabilization against decomposition initiated by iron.

There have been several disclosures of stabilizing systems for stabilization of various halogenated hydrocarbons, particularly methyl chloroform. It is well recognized in the art, however, that good stabilization of one type of halogenated hydrocarbon is no indication of successful stabilization against other halogenated hydrocarbons, since the nature and degree of the decomposition reaction is greatly different for each of the different halogenated hydrocarbons. For instance, the Brown reference, U.S. Pat. No. 3,049,571, discloses that methyl chloroform can be stabilized against vapor phase decomposition caused by contact with zinc by the combination of nitromethane, s-butyl alcohol, 1,4-dioxane, or monohydric acetylenic alcohol with a vicinal, aliphatic epoxide. Brown, however, does not disclose the problems inherent in the stabilization of 1,1,1-trichloroethane against contact with iron, and Brown specially indicates recognition of the well-known fact that special problems exist with methyl chloroform which do not exist with other chlorinated solvents.

The Cormany, et al, U.S. Pat. Nos. 3,265,747 and 3,251,891, each disclose that methyl chloroform can be stabilized against vapor phase decomposition caused by contact with a light metal such as aluminum, magnesium or their alloys, by the use of one or more stabilizers selected from a list of several hundred possible stabilizers, which include selected aliphatic and aromatic epoxides, such as styrene oxide. Cormany, et al, however, do not disclose the problems inherent in the stabilization of 1,1,1-trichloroethane against contact with iron and likewise specifically indicate that methyl chloroform presents its own unique difficulties regarding stabilization so that experiences in the stabilization of other halogenated hydrocarbons are not applicable.

The Campbell, et al reference, U.S. Pat. No. 3,661,788, discloses that methyl chloroform can be stabilized against decomposition initiated by iron by stabilizing amounts of pyran type compounds or mixtures thereof with auxiliary stabilizers such as various epoxides including aliphatic epoxides containing 3 – 6 carbon atoms. However, the stabilizing combinations of Campbell, et al differ from those of the present invention and do not stabilize methyl chloroform against iron as effectively as the stabilizing combination of the present invention.

A need exists, therefore, for a stabilization system for 1,1,1-trichloroethane against iron-initiated decomposition.

SUMMARY OF THE INVENTION

Accordingly, it is one object of this invention to provide a stabilization system to inhibit metal-initiated decomposition of 1,1,1-trichloroethane, which could cause generation of corrosive hydrogen chloride.

It is another object of this invention to provide a stabilization system to inhibit iron-initiated decomposition of 1,1,1-trichloroethane.

Briefly, these and other objects of the invention, as hereinafter will become more readily apparent, can be attained by the use of a stabilizing amount of styrene oxide, phenyl glycidyl ether or mixtures thereof in combination with a conventional 1,1,1-trichloroethane stabilizer of an alcohol, a nitro compound or a cyclic ether.

DETAILED DESCRIPTION OF THE INVENTION

Suitable conventional stabilizers which can be used with the stabilizer of this invention include the primary, secondary or tertiary alcohols, such as butanol, t-butanol; 1 – 3 carbon atom aliphatic nitro compounds, such as nitromethane and cyclic ethers such as dioxane and dioxolane.

The secondary or conventional stabilizer may be used in effectively stabilizing amounts of 1 to 10 vol. %, preferably 2 to 7 vol. %, and most preferably 3 to 5 vol. %.

The styrene oxide, phenyl glycidyl ether or mixtures thereof may be used in amounts of 0.001 – 10 vol. %, preferably 0.003 – 0.5 vol. % to 1,1,1-trichloroethane.

In practice, however, less than 0.03% by volume may be adequate.

A preferred combination of stabilizers is the combination of at least one of the stabilizers of the present invention with a conventional cyclic ether wherein the amount of ether ranges from 1 – 10 vol. %, preferably 2 – 8 vol. %, and most preferably 3 – 5 vol. %. When alcohols or nitro compounds are used as the conventional stabilizer in the stabilizer combination of the present invention, the amounts of each conventional stabilizer used range from 1 – 10 vol. % and 0.1 – 5 vol. %, respectively.

A preferred stabilizer combination is the combination of styrene oxide, phenyl glycidyl ether or mixtures thereof with cyclic ethers such as 1,4-dioxane, 1,3-dioxolane or the like.

Having now generally described the invention, a further understanding can be attained by reference to certain specific Examples which are included herein for purposes of illustration only and are not intented to be limiting unless otherwise specified.

COMPARISON EXAMPLES 1 – 11 AND EXAMPLES 1 – 7

An iron sample (13 mm. × 7.6 mm.), the surface of which had been well ground, was washed and dried and placed in a ground conical flask of 125 cc. capacity, and 25 cc. of 1,1,1-trichloroethane and various stabilizer systems were added to the contents. A reflux condenser was attached to the flask, then the mixed solution was heated in a water bath up to the boiling point, and the metallic sample was brought into contact with both the vapor and the liquid phases of 1,1,1-trichloroethane. After a lapse of time, the flask was removed from the water bath. The coloring of the liquid was observed and checked, and the contents of hydrochloric acid generated was quantitatively analyzed by titration. The results are shown in Table 1.

TABLE 1

| | Stabilizer | Amount (vol. %) | Hour | Liquid condition | HCl conc. (ppm) |
|---|---|---|---|---|---|
| COMPARISON | | | | | |
| 1. | tert-butanol | 1.5 | 10 | Yellow | 21 |
| 2. | nitroethane | 2.0 | 50 | " | 45 |
| 3. | dioxane | 4.0 | 50 | Light Yellow | 8 |
| 4. | nitromethane | 2.0 | 70 | " | 10 |
| 5. | 1,2-butylene oxide | 0.1 | 70 | " | 6 |
| 6. | tert-butanol | 3.0 | | | |
| | 1,2-butylene oxide | 0.1 | 70 | " | 10 |
| 7. | dioxane | 2.0 | | | |
| | 1,2-butylene oxide | 0.5 | 70 | " | 5 |
| 8. | tert-butanol | 3.0 | | | |
| | nitromethane | 1.0 | 50 | Yellow | 32 |
| 9. | dioxane | 2.0 | | | |
| | nitroethane | 0.5 | 50 | Light Yellow | 12 |
| 10. | tert-butanol | 2.0 | | | |
| | dioxane | 2.0 | 50 | Yellow | 15 |
| 11. | 2,3-dihydropyran | 3.0 | | | |
| | | | 70 | Light Yellow | 4 |
| EXAMPLE | styrene oxide | 0.03 | | | |
| 1. | dioxane | 2.0 | | | |
| | | | 70 | Clear | 0.1 |
| | styrene oxide | 0.03 | | | |
| 2. | dioxane | 2.0 | | | |
| | | | 70 | " | 1.0 |
| | phenyl glycidyl ether | 0.03 | | | |
| 3. | dioxane | 3.0 | | | |
| | nitromethane | 0.5 | 70 | " | 0.5 |
| | phenyl glycidyl ether | 0.5 | | | |
| 4. | dioxane | 3.0 | | | |
| | nitromethane | 0.5 | 70 | Clear | 0.8 |
| | styrene oxide | 0.005 | | | |
| 5. | dioxane | 3.0 | | | |
| | styrene oxide | 0.03 | 70 | " | 0.4 |
| | phenyl glycidyl ether | 0.45 | | | |
| 6. | 1,3-dioxolane | 7.0 | | | |
| | styrene oxide | 0.03 | 70 | " | 1.0 |
| | phenyl glycidyl ether | 0.03 | | | |
| 7. | 1,4-dioxane | 5.0 | | | |
| | | | 70 | " | 0.3 |
| | styrene oxide | 0.02 | | | |

Having now fully described the invention, it will be apparent to one of ordinary skill in the art that many changes and modifications can be made thereto without departing from the spirit or scope of the invention.

Accordingly, what is claimed as new and intended to be covered by Letters Patent is:

1. A stabilized 1,1,1-trichloroethane which is stabilized against decomposition initiated by contact with iron, which comprises:

the admixture of 1,1,1-trichloroethane and 0.001–10 volume percent of a stabilizer selected from the group consisting of styrene oxide, phenylglycidyl ether and mixtures thereof and a second stabilizer selected from the group consisting of a primary, secondary or tertiary alkanol, a 1–3 carbon atom aliphatic nitro compound, 1,4-dioxane or 1,3-dioxolane and mixtures thereof in amounts efficient to effectively stabilize said trichloroethane.

2. The stabilized trichloroethane of claim 1, wherein said second stabilizer is 1,4-dioxane or 1,3-dioxolane.

3. The stabilized trichloroethane of claim 1, wherein said 1,4-dioxane or 1,3-dioxolane is used in amounts of 1 – 10 vol. %.

4. The stabilized trichloroethane of claim 3, wherein said 1,4-dioxane or 1,3-dioxolane is used in amounts of 2 – 8 vol. %.

5. The stabilized trichloroethane of claim 1, wherein the effective stabilizing amount of said alkanol is 1 – 10 vol. %.

6. The stabilized trichloroethane of claim 1, wherein the effective stabilizing amount of said nitro compound is 0.1 – 5 vol. %.

7. A stabilized 1,1,1-trichloroethane which is stabilized against decomposition initiated by contact with iron, which comprises:

the admixture of 1,1,1-trichloroethane and 0.001–10 volume percent of a stabilizer selected from the group consisting of styrene oxide, phenylglycidyl ether and mixtures thereof and a second stabilizer selected from the group consisting of butanol, or t-butanol, a 1–3 carbon atom aliphatic nitro compound, 1,4-dioxane or 1,3-dioxolane and mixtures thereof in amounts sufficient to effectively stabilize said trichloroethane.

* * * * *